United States Patent [19]

Granz et al.

[11] Patent Number: 5,269,292
[45] Date of Patent: Dec. 14, 1993

[54] PRESSURE PULSE SOURCE HAVING A POSITIVE LENS WITH A PRESSURE SENSOR

[75] Inventors: Bernd Granz, Oberasbach; Georg Koehler, Geisfeld; Ulrich Schaetzle, Erlangen, all of Fed. Rep. of Germany

[73] Assignee: Siemens Aktiengesellschaft, Munich, Fed. Rep. of Germany

[21] Appl. No.: 759,664

[22] Filed: Sep. 13, 1991

[30] Foreign Application Priority Data

Oct. 30, 1990 [DE] Fed. Rep. of Germany ....... 4034533

[51] Int. Cl.$^5$ .............................................. A61B 17/22
[52] U.S. Cl. .................. 128/24 EL; 367/150; 367/175
[58] Field of Search ........ 128/24 AA, 24 EL, 660.03; 367/138, 150, 175

[56] References Cited

U.S. PATENT DOCUMENTS

| | | |
|---|---|---|
| 4,674,505 | 6/1987 | Pauli et al. . |
| 4,725,989 | 2/1988 | Granz et al. . |
| 4,834,074 | 5/1989 | Reichenberger . |
| 5,009,232 | 4/1991 | Hassler et al. . |

FOREIGN PATENT DOCUMENTS

| | | |
|---|---|---|
| 2719119 | 1/1978 | Fed. Rep. of Germany . |
| G8622086 | 6/1988 | Fed. Rep. of Germany . |
| 3703338 | 8/1988 | Fed. Rep. of Germany . |
| 2722252 | 11/1988 | Fed. Rep. of Germany . |
| 3739390 | 6/1989 | Fed. Rep. of Germany . |

Primary Examiner—Ruth S. Smith
Attorney, Agent, or Firm—Hill, Steadman & Simpson

[57] ABSTRACT

A pressure pulse source, of the type suitable for generating shockwaves, has a positive lens for focusing the pressure pulses onto a focal zone. The positive lens has an acoustic exit face which has a shape, in a focusing zone, for focusing the pressure pulses and a shape, in at least one measurement zone, which deviates from the shape in the focusing zone. A pressure sensor containing a piezoelectric polymer foil is disposed at the measurement zone. The pressure sensor, or a number of such pressure sensors, generate signals which are used to monitor the pressure pulses emerging from the positive lens, such as by acquiring their peak value.

19 Claims, 3 Drawing Sheets

PRESSURE PULSE SOURCE HAVING A POSITIVE LENS WITH A PRESSURE SENSOR

BACKGROUND OF THE INVENTION

1. Field of the Invention

The present invention is directed to a pressure pulse source having a positive lens for focusing the pressure pulses onto a focal zone, and having at least one pressure sensor containing a piezoelectric polymer foil applied to the surface of the positive lens which forms the sound exit face.

2. Description of the Prior Art

A pressure pulse source is disclosed in European Application 0 229 981 having a plurality of pressure sensors arranged on the sound exit face of a positive lens which focuses the pressure pulses onto a focal zone. The pressure sensors identify properties of the focal zone, such as the dimensions thereof, particularly during operation of the pressure pulse source. The measured values supplied by the pressure sensors are compared to rated (desired) values which correspond to a focal zone having defined dimensions. Other important information which may be useful in the operation of the pressure pulse source, however cannot be acquired using this known pressure pulse source, or cannot be acquired with adequate precision. Such information includes, for example, information about the chronological curve of the pressure pulse and the peak value of the pressure of the pressure pulse emerging from the positive lens. Such information also includes information as to whether the pressure pulse source is aligned relative to a subject to be acoustically irradiated so that the subject, or a defined region of the subject, is situated in the focal zone.

Particularly given utilization of a pressure pulse source for medical purposes, for example for non-invasive disintegration of calculi, information of this type is of basic significance for the safety of the patient, and thus such information must be constantly available during operation of the pressure pulse source. Knowledge of the chronological curve of the pressure of the pressure pulse emerging from the positive lens permits exact conclusions to be drawn regarding the peak pressure to be anticipated in the focal zone, which should not be any higher than absolutely necessary in order to avoid unnecessary tissue damage. Moreover, the region to be acoustically irradiated should always be precisely situated in the focal zone of the pressure pulses, so as to avoid unnecessary damage to surrounding tissue.

SUMMARY OF THE INVENTION

It is an object of the present invention to provide a pressure pulse source having a positive lens for focusing the pressure pulses onto a focal zone with at least one pressure sensor containing a piezoelectric polymer foil applied to the surface of the positive lens forming the sound exit face thereof, wherein the peak value or the chronological curve of the pressure of the pressure pulses can be obtained during operation of the pressure pulse source, and/or monitoring of the alignment of the pressure pulse source relative to the subject to be acoustically irradiated can be undertaken during operation of the pressure pulse source.

The above object is achieved in accordance with the principles of the present invention in a pressure pulse source having a positive lens, which serves the purpose of focusing the generated pressure pulses onto a focal zone, which has at least one focusing zone and at least one measurement zone. The surface of the positive lens forming the sound exit face has a shape in the measurement zone which deviates from the shape in the focusing zone, the shape in the focusing zone being the shape required for the focusing of the pressure pulses. A pressure sensor containing a piezoelectric polymer foil is applied in the measuring zone to the surface of the positive lens which forms the sound exit face. The surface of the positive lens forming the sound exit face in the focusing zone thus retains undisturbed the shape required for exact focusing of the pressure pulses to the focal zone, and the positive lens is shaped in the region of the measurement zone so as to optimally correspond to the task of measuring implemented with the pressure sensor.

In an embodiment of the invention a pressure sensor for identifying the peak value or the chronological curve of the pressure of the pressure pulses is applied on a surface proceeding substantially at a right angle relative to the acoustic propagation direction, i.e., the acoustic propagation direction which is present in the region of the polymer foil in the pressure sensor. An evaluation circuit for the signals supplied by the pressure sensor can be provided which calculates the chronological curve of the signals, or at least their peak values, and a graphic display can be provided for portraying the chronological curve. A numerical display can be provided for displaying the peak values. The chronological curve or the peak value of the pressure of a pressure pulse emerging from the positive lens can thus be calculated from the pressure sensor signals, with measuring errors being substantially excluded becuase of the arrangement of the pressure sensor on a surface proceeding at a right angle to the sound propagation direction. This is also important in view of the precise reproduction of the chronological curve of the pressure pulse, since a pressure sensor arranged at some other angle with respect to the sound propagation direction would supply signals (due to the fact that it has a finite area) which would simulate a time duration which would be lengthened in comparison to the actual conditions, and would also simulate a decreased rise steepness and peak amplitude of the pressure pulse.

Because a continuous and reliable monitoring of the properties of the pressure pulses introduced into the patient is indispensable for the safety of the patient, an embodiment of the invention includes at least three pressure sensors, and the evaluation stage compares the peak values of the signals supplied by the respective pressure sensors and activates a warning means when at least two of the peak values do not substantially coincide. It is thus assured that, given malfunction of one or more pressure sensors, the operating personnel will be informed that a reliable monitoring of the properties of the pressure pulses is no longer insured.

In a preferred version of the pressure pulse source, at least three measurement zones are provided. The pressure sensors in the measurement zones serve the purpose of aligning the pressure pulse source and the subject to be acoustically irradiated relative to each other by means of the pressure sensors detecting and measuring the reflected portions of the pressure pulses from the subject. The pressure sensors, formed of polymer foil, are substantially spherically curved around the focal zone, the surfaces of the respective pressure sensors which are irradiated by the reflected portions of the pressure pulses preferably having the same radius of curvature. An evaluation stage for the signals generated by the pressure sensors is provided which evaluates the differences in transit time which occur between the output signals of the pressure sensors which are associated with the same pressure pulse. Given the incidence of a pressure pulse onto a boundary surface at which an acoustic impedance discontinuity exists, for example given incidence onto the surface of a calculus, a diffracted wave which propagates spherically departs from the boundary surface. The parts of the diffracted wave which proceed to the individual pressure sensors cause corresponding output signals of those pressure sensors, with the respective transit times from the calculus to each of the pressure sensors having a characteristic relationship relative to each other when the diffracted wave emanates from the focal zone of the pressure pulses. If, for example, all of the pressure sensors are arranged on surfaces spherically curved around the focal zone having the same radius of curvature, the transit times will be substantially identical when the calculus is situated in the focal zone. By evaluating the differences in transit time, therefore, an identification can be made as to whether a subject to be acoustically irradiated, for example a calculus, which has an acoustic impedance differing from that of the surrounding medium, is situated in the focal zone of the pressure pulse source. It is important that the pressure sensors be applied on surfaces spherically curved around the focal zone, because the pulse duration of the output signals of the pressure sensors would otherwise be lengthened, and the rise steepness and the peak value of the output signals would thus be diminished. The decrease in the rise steepness and in the peak value, however, would in particular cause a sufficiently exact calculation of the differences in transit time to be no longer possible, given differences in the transit time of, for example, 10 $\mu$s. Such a difference in transit time corresponds to a difference in actual travel of the wave of 1.5 cm in human tissue.

In a further embodiment of the invention, means are provided for adjusting the position of the pressure pulse source and a subject to acoustically irradiated relative to each other. The evaluation stage actuates the adjustment means so that the differences in transit time are maintained in a relationship to each other which corresponds to a desired alignment of pressure pulse source and the subject. It is thus insured in a simple manner that the desired alignment of pressure pulse source and the subject is always established. It is preferable in this context to use four pressure sensors, arranged on the corners of a square, with a straight line, extending from a center of the square normal to the plane of the square, proceeding through the focal zone. If the pressure pulse source and the subject to be acoustically irradiated are movable relative to each other in the directions of the axes of a rectangular coordinate system, and if the axes of the coordinate system coincide with the diagonals of the square and the aforementioned straight line, the correct position of the pressure pulse source and the subject relative to each other with respect to two of the adjustment axes can be produced in a simple manner. First, the pressure pulse source is adjusted in the direction of one diagonal of the square until the difference in the transit time between the corresponding pressure sensors for that diagonal is zero. Next, the pressure pulse source is adjusted in position along the other diagonal of the square, until the difference in the transit time between the signals of the pressure sensors associated with that diagonal is zero.

Polyvinylidenefluoride (PVDF) is particularly suited for the material of the piezoelectric polymer foil.

DESCRIPTION OF THE PREFERRED EMBODIMENTS

Figure 1:
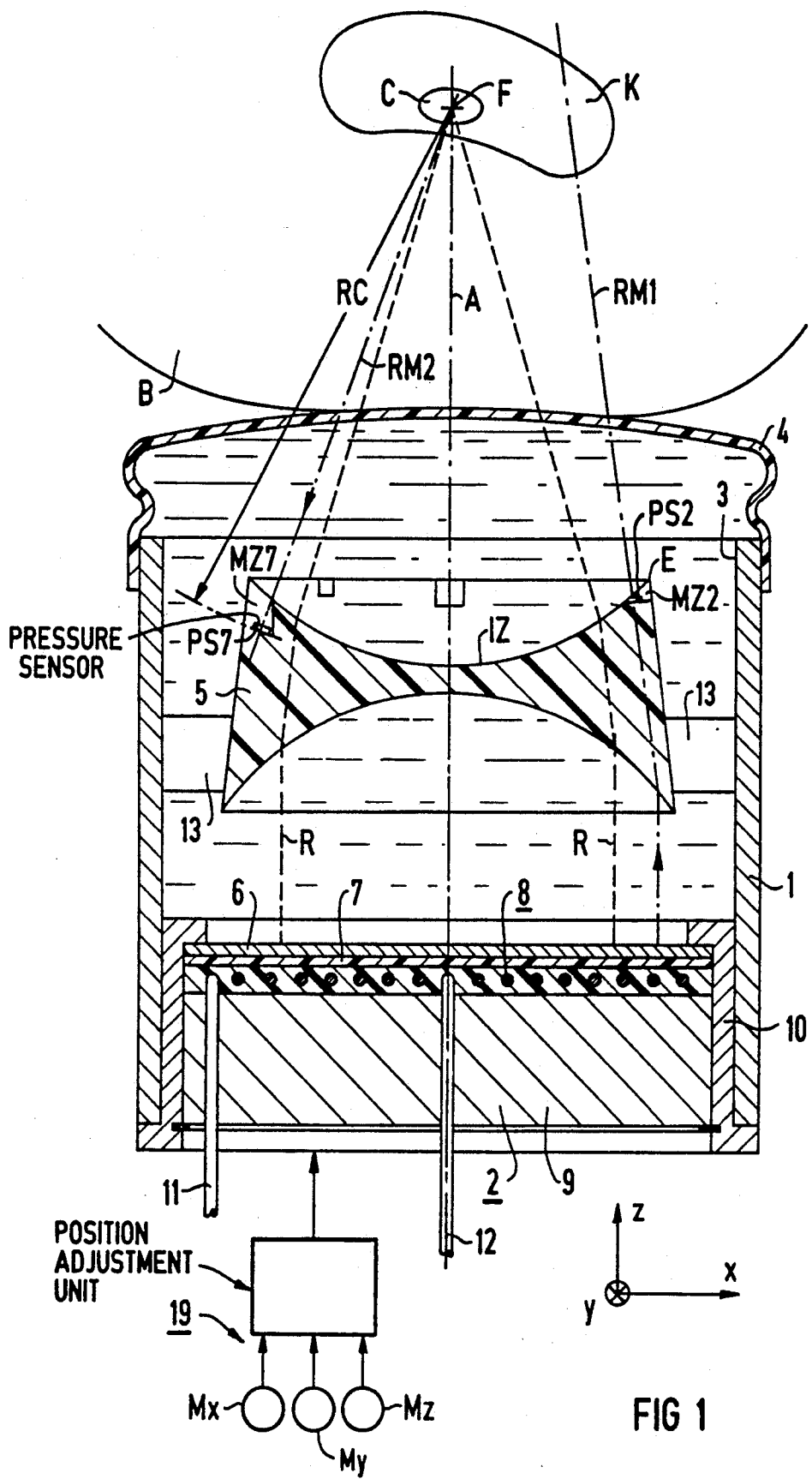
FIG. 1 is a longitudinal section taken through line I—I of FIG. 2 of a shockwave source constructed in accordance with the principles of the present invention, with associated components being shown schematically.

A shockwave source constructed in accordance with the principles of the present invention is shown in FIG. 1, having a tubular housing 1 with a shockwave generator, generally referenced 2, disposed at one end. An exit opening 3 for pressure pulses emanating from the shockwave generator 2 is disposed at the opposite end of the housing 1. The exit opening 3 is covered with a flexible sack 4. The space surrounded by the shockwave generator 2, the housing 1 and the flexible sack 4 contains water as the acoustic propagation medium for the pressure pulses emanating from the shockwave source 2. The pressure pulses gradually intensify over their propagation path to form shockwaves as a consequence of the non-linear compression properties of the propagation medium. For simplicity, the term "shockwave" will be used below, regardless of whether a pressure pulse has in fact intensified to form a shockwave.

An acoustic positive lens 5 is disposed in the propagation medium for focusing the shockwaves emanating from the shockwave generator 2. The positive lens 5 focuses the shockwaves onto a focal zone disposed on the acoustic axis A of the shockwave source, which is coincident with the center axis of the shockwave source. The center point of the focal zone is referenced F, and is the point of intersection for arbitrarily selected boundary lines R.

The shockwave source can be pressed against a schematically-indicated body B of a patient by means of the flexible sack 4, for the purpose of acoustic coupling. The shockwave source is aligned such that a calculus C to be disintegrated, for example the stone of a kidney K in the body B of the patient, is situated in the focal zone. This is accomplished in known manner using a location system (not shown) which may be an x-ray system or an ultrasound system, such as an ultrasound system containing an ultrasound sector applicator.

The shockwave generator 2 shown in the exemplary embodiment of FIG. 1 is an electromagnetic or electrodymanic shockwave generator, of the type disclosed in greater detail U.S. Pat. No. 4,674,505. The shockwave generator 2 has a planar membrane 6 in the form of a circular disc and consisting of electrically conductive material. One side of the membrane 6 is immediately adjacent to the water contained in the shockwave source. A planar spiral coil 8 is disposed on the opposite side of the membrane 6, with an insulating foil 7 therebetween. The coil 8 is mounted on a coil carrier 9 consisting of electrically insulating material. An electrically insulating casting compound is disposed between the spiral turns of the coil 8. The components of the shockwave generator 2 are held in axially non-displaceable manner in the bore of a mounting ring 10, which is in turn held axially non-displaceably in the housing 1.

Figure 4:
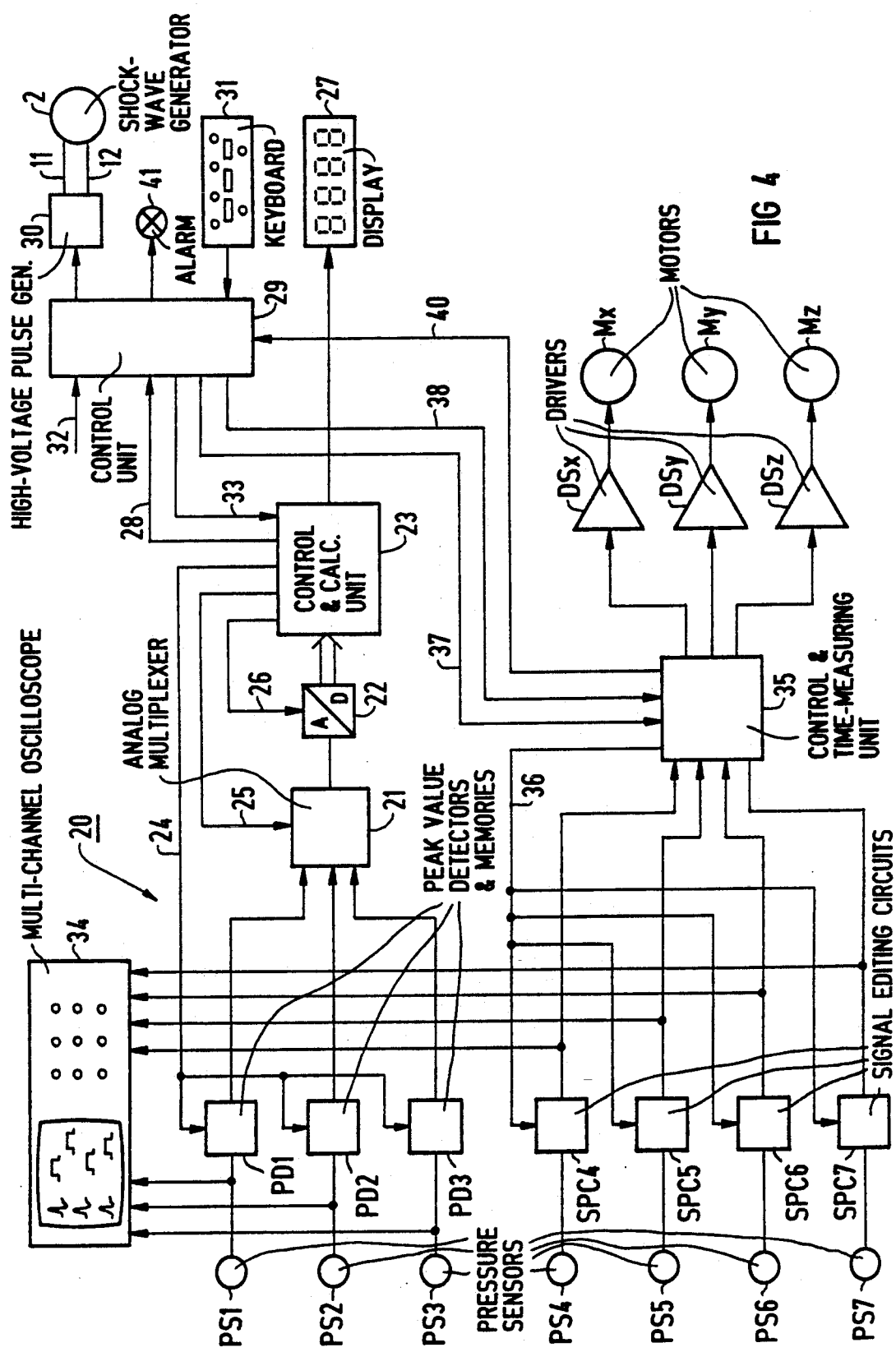
FIG. 4 is a schematic block diagram of components forming, and associated with, the signal evaluation stage for a shockwave source constructed in accordance with the principles of the present invention.

The coil 8 has two terminals 11 and 12 which are connected to a high-voltage pulse generator (shown in FIG. 4, but not shown in FIG. 1). The high-voltage pulse generator charges the coil 8 with high-voltage pulses, causing the coil 8 to generate a magnetic field extremely quickly. As a result, a current is induced in the membrane 6 which is opposite in direction to the current flowing in the coil 8, and which consequently generates an opposing magnetic field. The repelling interaction of the respective magnetic fields generated by the coil 8 and the membrane 6 cause the membrane 6 to be suddenly moved away from the coil 8. A planar shockwave is thereby introduced into the water contained in the shockwave source.

An acoustic positive lens 5 is provided for focusing the planar shockwaves. In the embodiment of FIG. 1, the lens 5 is a biconcave lens which is substantially rotationally symmetric relative to the acoustic axis A. The lens 5 consists of a material, for example polystyrol, in which the speed of sound is higher than in the water which is provided as the acoustic propagation medium. The positive lens 5 is mounted in the housing 1 by a plurality of support arms 13, two of which can be seen in FIG. 1.

Figure 2:
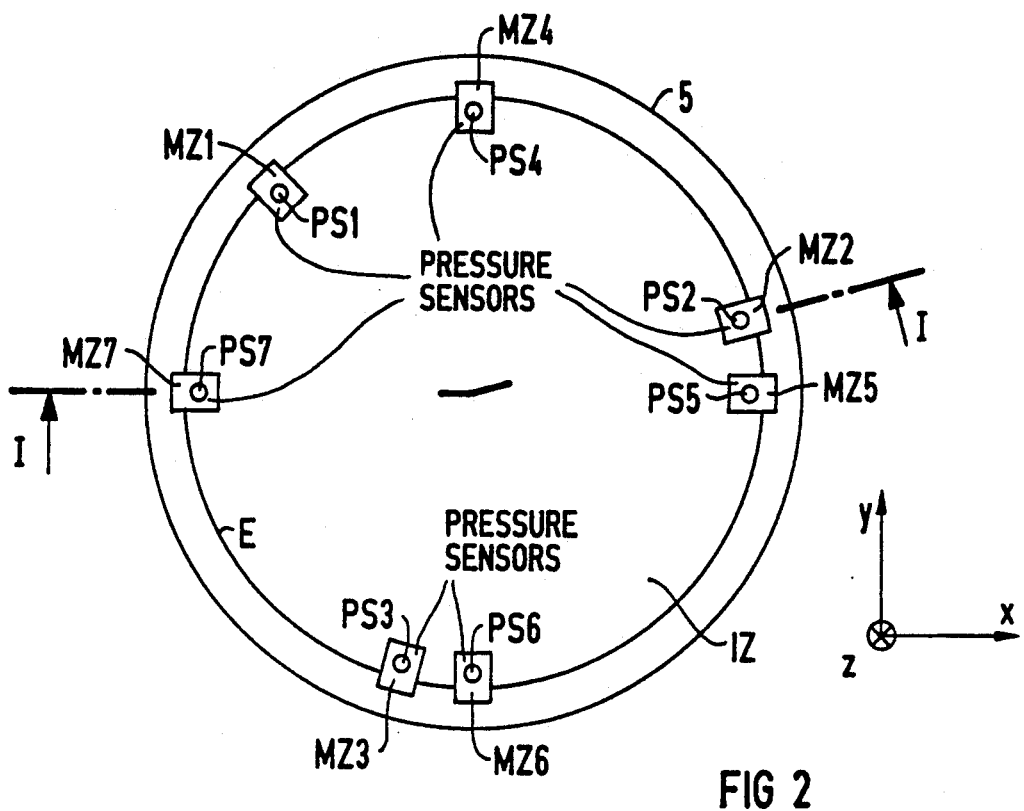
FIG. 2 is a plan view of the positive lens of the shockwave source shown in FIG. 1.

As described in more detail in connection with FIG. 2, the positive lens 5 is divided into a focusing zone IZ and into a plurality of measurement zones. In the embodiment of FIG. 1, there is a total of seven measurement zones MZ1 through MZ7. The focusing zone IZ and the measurement zones MZ1 through MZ7 are provided on the sound exit face of the positive lens 5, i.e., the side thereof facing away from the shockwave generator 2. The focusing zone IZ is that region of the positive lens 5 which is shaped for focusing the shockwaves. Since the laws of geometrical optics are also valid for acoustic waves, such focusing is accomplished, as is known, by appropriate shaping of the entry face of the lens 5, facing toward the shockwave generator 2, and shaping of the exit face, facing toward the focal zone. The regions of the exit face of the positive lens 5 at which the measurement zones MZ1 through MZ7 are located deviate from the shape required for focusing the shockwaves onto the focal zone. At these locations, respective pressure sensors PS1 through PS7, schematically indicated in FIGS. 1 and 2, are located.

The measurement zones MZ1 through MZ3, which are identical, are offset by 120° relative to each other with reference to the acoustic axis A. These measurement zones MZ1 through MZ3 each have a planar surface on which the pressure sensors PS1 through PS3 are respectively mounted. The respective planar surfaces proceed at a right angle relative to the acoustic propagation direction of that part of the shockwave emerging from the positive lens 5 in the region of each planar surface. This is shown in FIG. 1 with respect to the measurement zone MZ2 and a schematically indicated "ray" RM1, which indicates a part of the shockwave propagating through the measurement zone MZ2.

Each of the measurement zones MZ4 through MZ7 has a spherically curved surface, on which respective pressure sensors PS4 through PS7 are mounted. The spherically curved surfaces each have a radius of curvature with a center which is coincident with the center F of the focal zone. All of these spherical surfaces have the same radius of curvature RC, as indicted in FIG. 1 for the measurement zone MZ7. As indicated by the example of the "ray" RM2 in FIG. 1, this results in a straight line proceeding through the center F of the focal zone being disposed at a right angle on the respective spherically curved surface. The measurement zones MZ4 through MZ7 are identically fashioned. The zones MZ4 through MZ7 are arranged offset by 90° relative to each other with reference to the acoustic axis A. An angular spacing of 45° is present between the measurement zone MZ1 and the measurement zone MZ7. All of the measurement zones MZ1 through MZ7 are formed as recesses in the rim edge E of the positive lens 5 which faces away from the shockwave generator 2.

A schematically-indicated position adjustment unit 19 is shown in a schematically indicated operative connection to the shockwave source 1 in FIG. 1. The position adjustment unit 19 includes electric motors Mx, My and Mz. The adjustment unit 19 also includes gearings and associated components which serve in a known manner to adjust the position of the shockwave source in the directions of the axes of a three-dimensional rectangular, coordinate system, entered in FIGS. 1 and 2. The motor Mx is thus responsible for adjustment in the direction of the x-axis, the motor My is responsible for adjustment in the direction of the y-axis, and the motor Mz is responsible for adjustment in the direction of the z-axis of the coordinate system. The z-axis corresponds to the acoustic axis A, whereas the x-axis proceeds centrally through the measurement zones MZ5 and MZ7, and the y-axis proceeds centrally through the measurement zones MZ4 and MZ6. The pressure sensors PS4 through PS7 thus respectively lie on the corners of a square having a center through which the acoustic axis A proceeds (the central axis A also proceeding through the focal zone, as noted above).

Figure 3:
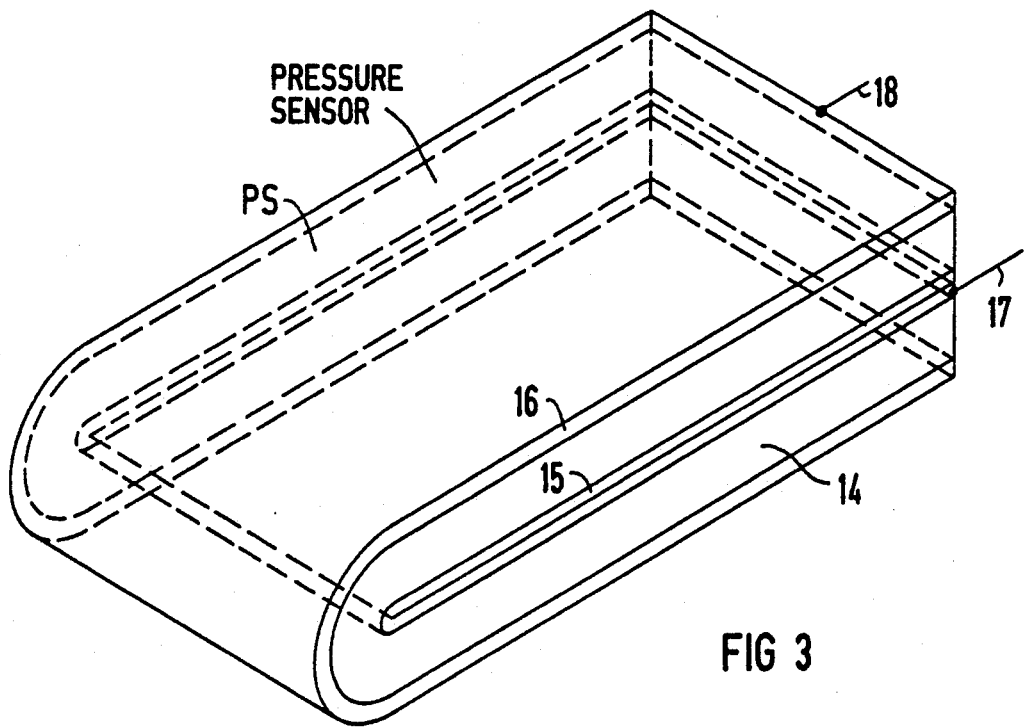
FIG. 3 is a schematic perspective view of a pressure sensor for use in the shockwave source constructed in accordance with the principles of the present invention.

One of the pressure sensors PS is shown in FIG. 3, all of the pressure sensors being identically fashioned. Each pressure sensor is formed by a piezoelectrically activated polymer foil of the type distributed by the Pennwalt Company of Great Britain under the designation Kynar ®-piezo-film SDT1-028k. The piezo foil 14 is provided with electrodes 15 and 16 on both sides, each of which consists of an electrically conductive layer, for example a metallic layer. The piezo foil 14 provided with the electrodes 15 and 16 is folded U-shaped so that the sides of the electrode 15 facing toward each other press against each other. The electrode 15 is electrically connected to a line 17 and the electrode 16 is connected to a line 18, the lines 17 and 18 leading to an evaluation stage, described in detail below.

The functioning of such known pressure sensors is such that an alternating charge signal is generated by the influence of shockwaves on the sensor, the alternating charge being acquired from piezo foil 14 by the electrodes 15 and 16. If polystyrol is used as the material for the positive lens 5 and water is used as the acoustic propagation medium, the acoustic impedance of the piezo foil 14 will be substantially matched to the acoustic impedances of these materials, and if the electrodes 15 and 16 are extremely thin, only weak reflections will occur at the boundary surfaces between the positive lens 5 and the pressure sensors PS1 through PS7, as well as at the boundary surfaces between the pressure sensors PS1 through PS7 and the water. These reflections will be substantially unseen in the output signals of the pressure sensors PS1 through PS7.

The pressure sensors PS1 through PS7 formed by polymeric piezo foil in this manner also offer the advantage that, due to their high deformability, they can be easily secured, for example by gluing, onto the spherically curved surfaces which are provided in the regions of the measurement zones MZ4 through MZ7. It has also been shown that such pressure sensors are extremely durable and generate output signals having amplitudes on the order of magnitude of a few volts, so that an extremely good signal-to-noise ratio is achieved.

The pressure sensors PS1 through PS3 allocated to the measurement zones MZ1 through MZ3 serve the purpose of measuring the chronological curve and the peak value of the pressure of those respective parts of the shockwave emerging from the positive lens 5 in the regions of the measurement zones MZ1 through MZ3. It is thus possible to continuously monitor the functioning of the shockwave source with respect to characteristic quantities of the generated shockwaves, so that potential malfunctions of the shockwave source can be recognized at an extremely early stage. It is also possible to make conclusions about the conditions in the focal zone from the measured characteristic quantities of the shockwaves, which is of special significance in the interest of patient safety. It is preferable to undertake a calibration of the pressure sensors PS1 through PS3, so that the pressure can be measured not only qualitatively, but also quantitatively.

The pressure sensors PS4 through PS7 allocated to the measurement zones MZ4 through MZ7 identify differences in the transit time between the respective parts of the diffracted substantially spherical wave which proceeds from the calculus C to be disintegrated after a shockwave is incident on the calculus C. On the basis of these differences in transit time which, given the described arrangement and operation of the measurement zones MZ4 through MZ7, disappear when the calculus C is on the acoustic axis A, it is possible to monitor the alignment of the shockwave source relative to the calculus C, and to correct this alignment as necessary.

Measurement errors which would arise in the form of a lengthening of the pulse duration and a decrease in the rise steepness and in the peak values of the output signals of the pressure sensors PS1 through PS3 and PS4 through PS7 are avoided as a consequence of the above-described arrangement of these pressure sensors. Such errors are avoided with respect to the pressure sensors PS1 through PS3 by arranging those sensors on respective surfaces which proceed at a right angle relative to the sound propagation direction in the vicinity of those sensors. Such errors are avoided with respect to the sensors PS4 through PS7 by arranging those sensors on respective surfaces which are spherically curved around the center of the focal zone.

The evaluation circuitry for the output signals of the pressure sensors PS1 through PS7 is generally referenced in FIG. 4 as an evaluation stage 20, which is connected to the shockwave source 1, the pressure sensors PS1 through PS7 and to motors Mx, My and Mz of the position adjustment unit 19. The pressure sensors PS1 through PS3 are respectively connected to peak value detectors and memories PD1 through PD3. The output signals of the peak value detectors and memories PD1 through PD3 are supplied to the inputs of 3-to-1 analog multiplexer 21, having an output connected to the input of an analog-to-digital converter 22. The digital output data of the analog-to-digital converter 22 are supplied to a calculating and control unit 23. By means of control lines 24, 25 and 26, the calculating and control unit 23 controls the peak value detectors and memories PD1 through PD3, the analog multiplexer 21 and the analog-to-digital converter 22. This control is undertaken in manner such that the most recent peak value of the output signals of the pressure sensors PS1 through PS3 stored in the peak value detectors and memories PD1 through PD3 is erased immediately before a shockwave is generated with the shockwave generator 2. The analog multiplexer 21 successively supplies the peak values of the output signals of the pressure sensors PS1 through PS3, detected and stored by the peak value detectors and memories PD1 through PD3, to the analog-to-digital converter 22 a short time after the generation of a shockwave has ensued. This short time is at least equal to the transit time of a shockwave from the shockwave generator 2 through the positive lens 5. The corresponding digital data successively proceed to the control and calculating unit 23 in which the data are intermediately stored. The control and calculating unit 23 compares the calculated peak values to each other, and determines whether at least two of the calculated peak values substantially coincide. For example, the calculating and control unit 23 may determine that such substantial coincidence exists as long as the lower peak value deviates from the higher peak value by less than a maximum of 10%.

If at least two peak values substantially coincide, the control and calculating unit 23 calculates the average value of the substantially coinciding peak values, and multiplies this average value by a calibration factor stored in the control and calculating unit 23. This average value, obtained for the peak pressures measured by the pressure sensors PS1 through PS3 which substantially coincide, is portrayed on a display 27 connected to the control and calculating unit 23. A digital display is shown as an example in FIG. 4, however, an analog display may also be provided.

If the control and calculating unit 23 determines that a minimum of two of the peak values failed to substantially coincide, a signal is supplied via a line 28 to a control unit 29, which subsequently activates an alarm 41. As an example in the embodiment of FIG. 4, a light signal is shown as the alarm 41.

The high-voltage pulse generator 31, required for the operation of the shockwave source and connected to the shockwave generator 2 via terminals 11 and 12, is also connected to the control unit 29 via a control line. The control unit 29 activates the high-voltage pulse generator 30 to cause the release of high-voltage pulses, which in turn cause the generation of shockwaves. Activation of the high-voltage pulse generator 30 can optionally periodically ensue by means of the control unit 29, or can be undertaken manually by use of a keyboard 31 connected to the control unit 29. Such activation can also take place in a known manner, not shown in FIG. 4, by using a signal representing a periodic body function of the patient which can be supplied to the control unit 29 via an input 32.

The described procedures for calculating and storing the peak values of the output signals of the pressure sensors PS1 through PS3, the analog-to-digital conversion thereof, and the processing and display of the digital data, all obtained by the control and calculating unit 23, are repeated following the generation of each shockwave. The control and calculating unit 23 receives the clock signal required for this purpose from the control unit 29 via a line 33.

The output signals of the pressure sensors PS1 through PS3 are supplied to a multi-channel oscilloscope 34, which shows these signals vertically above one another in the left-half of its screen, so that a monitoring of the chronological curve of the pressure of the shockwaves is also possible.

The output signals of the pressure sensors PS4 through PS7 are respectively supplied to signal editing circuits SPC4 through SPC7. The signal editing circuits SPC4 through SPC7 are controlled by a control and time-measuring unit 35 via a control line 36 so that their respective inputs, upon the generation of a shockwave, are inhibited for a time which is at least equal to the transit time of the shockwave from the shockwave generator 2 through the positive lens 5, and which is not substantially longer than the transit time of the shockwave from the shockwave generator 2 to the calculus C to be disintegrated. The control and time-measuring unit 35 receives the clock signals required for this purpose from the control means 29 via a line 37. Only those parts of the output signals of the pressure sensors PS4 through PS7 which represent the diffraction wave emanating from the calculus C proceed to the editing circuits SPC4 through SPC7, after the calculus C is charged with a shockwave. These signal parts are converted into square-wave pulses having a defined duration in the identical signal editing circuits SPC4 through SPC7. The signal editing circuits SPC4 through SPC7 may each be constructed, for example, with a Schmitt trigger followed by a monoflop. The duration of the square-wave pulses is longer than the overall duration of the diffracted wave. This means that each diffracted wave can trigger the monoflops contained in the signal editing circuits SPC4 through SPC7 only a single time.

The square-wave pulses from the signal editing circuits SPC4 through SPC7 are supplied to the control and time-measuring unit 35. The control and time-measuring unit 35 measures the chronological duration by which the leading edges of the square-wave pulses from the signal editing circuits SPC5 and SPC7 are offset relative to one another. This chronological duration corresponds to the difference in transit time between those parts of the diffracted wave which proceed to the pressure sensors PS5 and PS7, which lie on the x-axis. The control and time-measuring unit 35 also measures the chronological duration by which the leading edges of the square-wave pulses from the signal editing circuits SPC4 and SPC6 are offset relative to one another. This chronological duration corresponds to the difference in transit time between the parts of the diffracted wave proceeding to the pressure sensors PS4 and PS6, disposed on the y-axis. Lastly, the control and time-measuring unit 35 measures the chronological duration which elapses between the activation of the shockwave generator 2 for generating a shockwave (a signal being supplied at the time of activation to the control and time-measuring unit 35 from the control unit 29) and the arrival of the leading edge of the square-wave pulse formed from the output signal of one of the pressure sensors PS4 through PS7, for example the pressure sensor PS4. The control and time-measuring unit 35 calculates the chronological difference between the chronological duration measured in this manner and a value stored in the control and time-measuring unit 35. The stored value corresponds to the sum of the transit times of the shockwave from the shockwave generator 2 to the calculus C, and the transit time of the diffracted wave from the calculus C to the pressure sensor PS4 when the calculus C is precisely situated in the focal zone.

On the basis of the data calculated in the above-described manner, the control and time-measuring and control unit 35 actuates the motors Mx, My and Mz of the adjustment unit 19 via respective drivers DSx, DSy and DSz so that the differences in the transit time of the diffracted wave to the pressure sensors PS4 and PS6, or to the pressure sensors PS5 and PS7, as well as the chronological difference between the stored value and the chronological duration between the generation of a shockwave and the arrival of the diffracted wave at the pressure sensor PS4, go to zero, or to a specified non-zero value. When these differences are zero, the shockwave source is precisely aligned along axis A to the calculus C to be disintegrated. If alignment at an angle relative to axis A is desired, the difference will be a non-zero value correlated with the desired angle. The time-measuring and control unit 35 can be set to cease operation of the motors Mx, My and Mz when the desired difference (zero or non-zero) is reached.

In order to achieve the necessary positioning to make these differences go to zero, the control and time-measuring unit 35 proceeds to drive the motors Mx and My with a step-by-step drive with a step width of, for example, 1 mm. The control and time-measuring unit 35 in this manner first aligns the shockwave source in the x-y plane following each shockwave, such that the aforementioned differences in transit time go to the desired value. The direction in which the adjustment is undertaken is determined by the operational sign of the transit time difference, which is recognized by the control and time-measuring unit 35 by determining whether the leading edge of the square-wave pulse from the sensor PS4 or from the pressure sensor PS6 arrives first, and whether the leading edge of the square-wave pulse from the sensor PS5 or PS7 arrives first. Thereafter, adjustment of the shockwave source is undertaken in z-direction, the adjustment direction being determined by the operational sign of the aforementioned calculated chronological difference, using the stored value.

To enable optical supervision of the alignment of the shockwave source relative to the calculus C, the output signals of the signal editing circuits SPC4 through SPC7 are supplied to a multi-channel oscilloscope 34, where the signals are portrayed vertically above one another in the right-half of the display screen in correct phase relation.

When the control and time-measuring unit 35 determines that one of the pressure sensors PS4 through PS7 is not operating, this being recognized by the absence of a square-wave pulse from the corresponding signal editing circuit, the control and time-measuring unit 35 forwards a corresponding signal via a line 40 to the control unit 29, which subsequently actuates the alarm 41.

It is apparent that the above-described alignment of the shockwave source relative to the calculus C using the output signals of the pressure sensors PS4 through PS7 can only serve the purpose of correcting slight deviations which occur during treatment. The original locating of the calculus C to be disintegrated must be undertaken before beginning the treatment, using an x-ray or an ultrasound locating system. It is also possible to locate the calculus C to be disintegrated using the output signals of the pressure sensors PS4 through PS7, before beginning treatment, however, to do so the shockwave source must be operated so that it generates low-intensity shockwaves, so that injury to the patient does not occur. Only after the calculus C has been located in this manner are shockwaves generated having an intensity sufficient to disintegrate the calculus C. Reduced intensity shockwaves can be generated, for example, by charging the shockwave generator 2 with high-voltage pulses having a reduced amplitude from the high-voltage pulse generator 30.

In the described exemplary embodiment, the positive lens 5 has only a single focusing zone IZ. It is possible, however, to provide a plurality of focusing zones.

As a result of the above-described structure of a shockwave generator constructed in accordance with the principles of the present invention many options are available in the operation of the apparatus. The generated pressure pulses can be monitored in terms of the peak value and/or the chronological curve of the pressure of those pulses, and monitoring of the alignment of the shockwave source relative to a subject to be acoustically irradiated can be undertaken during operation of the shockwave source in a simple manner.

In the exemplary embodiment set forth above, an electromagnetic or electrodynamic shockwave source has been shown as an example. Other pressure pulse sources, for example a piezoelectric pressure pulse source, may alternatively be used.

Although modifications and changes may be suggested by those skilled in the art, it is the intention of the inventors to embody within the patent warranted hereon all changes and modifications as reasonably and properly come within the scope of their contribution to the art.

We claim as our invention:

1. A pressure pulse source comprising:
   a housing containing an acoustic propagation medium;
   means in said housing for generating pressure pulses traveling in a path in a propagation direction in said acoustic propagation medium;
   a positive lens disposed in said housing in said path of said pressure pulses having a focusing zone and a measurement zone, said positive lens having a sound exit surface having a shape in said focusing zone for focusing said pressure pulses onto a focus zone and a shape in said measurement zone deviating from said shape in said focusing zone;
   a pressure sensor means, disposed in said measurement zone and including a pressure-sensitive element, for generating electrical signals corresponding to the interaction of said pressure pulses with said pressure sensor means; and
   means connected to said pressure sensor means for evaluating said electrical signals.

2. A pressure pulse source as claimed in claim 1 wherein said pressure sensor means is disposed on a surface in said measurement zone proceeding substantially perpendicularly relative to a propagation direction of said pressure pulses existing in the region of the pressure-sensitive element of said pressure sensor means.

3. A pressure pulse source as claimed in claim 2 wherein said evaluation means includes means for calculating a chronological curve of the pressure of said pressure pulses from said electrical signals of said pressure sensor means.

4. A pressure pulse source as claimed in claim 2 wherein said evaluation means includes means for calculating a peak value of each electrical signal from the pressure sensor means.

5. A pressure pulse source as claimed in claim 1 comprising three of said pressure sensor means and three measurement zones in which said three pressure sensor means are respectively disposed, and wherein said evaluation means includes means for comparing said peak values of said three pressure sensor means and for activating an alarm if a minimum of two of said peak values fail to substantially coincide.

6. A pressure pulse source as claimed in claim 1 comprising a plurality of said pressure sensor means and a like plurality of measurement zones, with each pressure sensor means being disposed on a surface in a respective measurement zone which is substantially spherically curved around said focal zone in the region of the pressure-sensitive element of the pressure sensor means.

7. A pressure pulse source as claimed in claim 6 wherein each of said surfaces has substantially the same radius of curvature.

8. A pressure pulse source as claimed in claim 6 wherein said evaluation means includes means for evaluating differences in transit time between respective electrical signals caused by a pressure pulse interacting in common with each pressure sensor means in said plurality of pressure sensor means.

9. A pressure pulse source as claimed in claim 8 further comprising:
   means for mechanically adjusting the position of said focus zone, relative to a subject to be acoustically irradiated by said pressure pulses, so that said differences in transit time are in a relationship corresponding to a desired alignment of said focus zone and said subject relative to each other.

10. A pressure pulse source as claimed in claim 6 wherein said plurality includes four pressure sensor means, and wherein said four pressure sensor means are respectively disposed in measurement zones at the corners of a square, a straight line passing through a center of said square and normal to the plane of said square proceeding through said focal zone.

11. A pressure pulse source as claimed in claim 1 wherein said pressure-sensitive element is a piezoelectric polymer foil.

12. A pressure pulse source as claimed in claim 11 wherein said piezoelectric foil is a polyvinylidenefluoride foil.

13. A pressure pulse source as claimed in claim 1 wherein said positive lens has a circumferential edge, and wherein said measurement zone is formed by a recess in said circumferential edge.

14. A pressure pulse source comprising:
   a housing containing an acoustic propagation medium;
   means in said housing for generating pressure pulses traveling in a path in a propagation direction in said acoustic propagation medium;
   a positive lens disposed in said housing in said path of said pressure pulses having a focusing zone and a plurality of measurement zones including a first group of measurement zones and a second group of measurement zones, said positive lens having a sound exit surface having a shape in said focusing zone for focusing said pressure pulses onto a focus zone and a shape in said measurement zones deviating from said shape in said focusing zone;

a plurality of pressure sensor means including a first group of pressure sensor means respectively disposed in said first group of measurement zones and a second group of pressure sensor means respectively disposed in said second group of measurement zones, each pressure sensor means containing a pressure-sensitive element, for generating respective electrical signals corresponding to the interaction of said pressure pulses with said pressure sensor means;

said first group of measurement zones each having a surface, on which a pressure sensor means is disposed, proceeding substantially perpendicularly relative to a propagation direction of said pressure pulses existing in the region of said pressure-sensitive element of the pressure sensor means in the measurement zone;

means connected to each of the pressure sensor means in said first group for receiving the electrical signals therefrom and for calculating at least one of a chronological curve of the pressure of said pressure pulses or a peak value of each electrical signal from the respective pressure sensor means in said first group;

each measurement zone in said second group of measurement zones having a surface, on which a pressure sensor means is disposed, which is substantially spherically curved around said focal zone in the region of said pressure-sensitive element of the pressure sensor means in the measurement zone;

means connected to each pressure sensor means in said second group for receiving the electrical signals therefrom for evaluating differences in transit time between respective electrical signals for a same pressure pulse from said pressure sensor means in said second group; and means for mechanically adjusting the position of said focus zone relative to a subject to be acoustically irradiated by said pressure pulses so that said differences in transit time have a relationship relative to each other corresponding to a desired alignment of said focus zone relative to said subject.

15. A pressure pulse source as claimed in claim 14 wherein said first group of pressure sensor means includes three pressure sensor means, and wherein said means for evaluating the electrical signals of said pressure sensor means in said first group includes means for comparing said peak values and means for activating an alarm if a minimum of two of said peak values fail to substantially coincide.

16. A pressure pulse source as claimed in claim 14 wherein each of said surfaces of said measurement zones in said second group has substantially the same radius of curvature.

17. A pressure pulse source as claimed in claim 14 wherein said pressure-sensitive element is a piezoelectric polymer foil.

18. A pressure pulse source as claimed in claim 17 wherein said piezoelectric polymer foil is a polyvinylidenefluoride foil.

19. A pressure pulse source as claimed in claim 14 wherein said positive lens has a circumferential edge, and wherein said measurement zones are formed by respective recesses in said circumferential edge.

* * * * *